United States Patent [19]

Lagosky

[11] Patent Number: 5,629,205

[45] Date of Patent: May 13, 1997

[54] PROMOTERS FOR GENE EXPRESSION

[75] Inventor: Peter A. Lagosky, Toronto, Canada

[73] Assignee: Allelix Biopharmaceuticals Inc., Ontario, Canada

[21] Appl. No.: 445,133

[22] Filed: May 19, 1995

[51] Int. Cl.$^6$ .......................... C12N 15/11; C12N 15/16; C12N 15/63

[52] U.S. Cl. .................. 435/320.1; 536/23.1; 536/23.51; 536/24.1

[58] Field of Search ....................... 435/320.1; 536/23.1, 536/23.51, 24.1

[56] References Cited

U.S. PATENT DOCUMENTS 5,362,646  11/1994  Bujard et al. ..................... 435/252.33

FOREIGN PATENT DOCUMENTS

| 1318271 | 5/1925 | Canada . |
| 0207459 | 6/1986 | European Pat. Off. . |
| 0357391 | 3/1990 | European Pat. Off. . |

OTHER PUBLICATIONS

Kristine De Sutter, et al.; "Production of enzymatically active rat protein disulfide isomerase in *Escherichia coli*"; Gene, 141, 1994, pp. 163–170.

Nicolas Groch, et al., "Synthesis of the *Bacillus subtilis* histone–like DNA–binding protein Hbsu in *Escherichia coli* and secretion into the periplasm"; Gene, 124, 1993, pp. 99–103.

John Ghrayeb, et al.; "Secretion cloning vectors in *Escherichia coli*"; The EMBO Journal, 3, 1984; pp. 2437–2442.

Hansen M. Hsiung, et al.; "Use of Bacteriocin Release Protein In E. Coli For Excretion of Human Growth Hormone Into the Culture Medium"; Biotechnology, vol. 7, Mar. 1989; pp. 267–271.

Hendy et al Proc. Natl. Acad Sci. USA, vol. 78, No. 12, pp. 7365–7369, Dec. 1981 "Nucleotide sequence of cloned cDNAs encoding human preproparathyroid hormone".

Miller et al Gene. 24 (1983) 309–315, Elsevier "Nucleotide sequence of the partition locus of *Escherichia coli* plasmid pSC101".

Bagdasarian et al. Gene. 26 (1983) 273–282, Elsevier "Activity of the hybrid trp–lac (tac) promoter of *Escherichia coli* in *Pseudomonas putida*. Construction of broad–host–range, controlled–expression vectors".

Tsung et al Proc. Natl. Acad Sci. USA, vol. 87, pp. 5940–5944, Aug. 1990 "Enhancement of RNA polymerase binding to promoters by a transcriptional activator, OmpR, in *Escherichia coli*: Its positive and negative effects on transcription".

Gentz et al J. Bacteriology, Oct. 1985, vol. 164, No. 1, pp. 70–77 "Promoters Recognized by *Escherichia coli* RNA Polymerase Selected by Function: Highly Efficient Promoters from Bacteriophage T5".

Hillen et al J. Mol. Biol, (1984) 172, 185–201 "Control of Expression of the Tn10–encoded Tetracycline Resistance Operon II. † Interaction of RNA Polymerase and TET Repressor with the tet Operon Regulatory Region".

*Primary Examiner*—Mindy Fleisher
*Assistant Examiner*—Terry A. McKelvey

[57] ABSTRACT

The present invention provides a novel expression system for the production of protein in bacterial hosts. The system utilizes novel promoters that are highly efficient in initializing transcription and therefore enhance protein yield. The promoters comprise the −35 region of the consensus *E. coli* promoter, the −10 region of the lppP-5 promoter and a spacer between these two regions derived from either the lpp or lacUV5 promoters.

20 Claims, 2 Drawing Sheets

5'-CTCGAGGCCACCCGGGCCAAAATTTATCAAA
TTGACAACATAAAAACTTTGTGTTATACT
GTCGACAATTGTGAGCGGATAACAATTTCACACAGAATTC-3'

Fig.2

5'-CTCGAGGCCACCCGGGCCAAAATTTATCAAA
TTGACACTTTATGCTTCCGGCTCGTATACT
GTCGACAATTGTGAGCGGATAACAATTTCACACAGAATTC-3'

Fig.3

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TTGACAACAT AAAAAACTTT GTGTTATACT        30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TTGACACTTT ATGCTTCCGG CTCGTATACT        30

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

ACATAAAAAA CTTTGTGT        18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CTTTATGCTT CCGGCTCG        18

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

ATTAAAGAGG AGAAATTAAG C                                                                                     21

( 2 ) INFORMATION FOR SEQ ID NO:6:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CTCGAGGCCA CCCGGGCCAA AATTTATCAA AAATATCTGC AGTTGACAAC ATAAAAACT       60

TTGTGTTATA CTGTCGACAA TTGTGAGCGG ATAACAATTT CACACAGAAT TCATTAAAGA     120

GGAGAAATTA AGCATG                                                                                          136

( 2 ) INFORMATION FOR SEQ ID NO:7:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CTCGAGGCCA CCCGGGCCAA AATTTATCAA AAATATCTGC AGTTGACAAC ATAAAAACT       60

TTGTGTTATA CTGTCGACAA TTGTGAGCGG ATAACAATTT CACACAGAAT TCAGGAGGAA     120

AAAATTATGA TG                                                                                              132

( 2 ) INFORMATION FOR SEQ ID NO:8:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CTCGAGGCCA CCCGGGCCAA AATTTATCAA AAATATCTGC AGTTGACACT TTATGCTTCC      60

GGCTCGTATA CTGTCGACAA TTGTGAGCGG ATAACAATTT CACACAGAAT TCATTAAAGA    120

GGAGAAATTA AGCATG                                                                                          136

( 2 ) INFORMATION FOR SEQ ID NO:9:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CTCGAGGCCA CCCGGGCCAA AATTTATCAA AAATATCTGC AGTTGACACT TTATGCTTCC      60

GGCTCGTATA CTGTCGACAA TTGTGAGCGG ATAACAATTT CACACAGAAT TCAGGAGGAA    120

AAAATTATGA TG                                                                                              132

( 2 ) INFORMATION FOR SEQ ID NO:10:

(i) SEQUENCE CHARACTERISTICS:
  (A) LENGTH: 136 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:10:

```
CTCGAGGCCA CCCGGGCCAA AATTTATCAA AAATATCTGC AGTTGACATT GTGAGCGGAT        60
AACAATTATA CTGTCGACAA TTGTGAGCGG ATAACAATTT CACACAGAAT TCATTAAAGA       120
GGAGAAATTA AGCATG                                                        136
```

(2) INFORMATION FOR SEQ ID NO:11:

(i) SEQUENCE CHARACTERISTICS:
  (A) LENGTH: 132 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:11:

```
CTCGAGGCCA CCCGGGCCAA AATTTATCAA AAATATCTGC AGTTGACATT GTGAGCGGAT        60
AACAATTATA CTGTCGACAA TTGTGAGCGG ATAACAATTT CACACAGAAT TCAGGAGGAA       120
AAAATTATGA TG                                                            132
```

(2) INFORMATION FOR SEQ ID NO:12:

(i) SEQUENCE CHARACTERISTICS:
  (A) LENGTH: 101 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:12:

```
CTCGAGGCCA CCCGGGCCAA AATTTATCAA ATTGACAACA TAAAAAACTT TGTGTTATAC        60
TGTCGACAAT TGTGAGCGGA TAACAATTTC ACACAGAATT C                           101
```

(2) INFORMATION FOR SEQ ID NO:13:

(i) SEQUENCE CHARACTERISTICS:
  (A) LENGTH: 101 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:13:

```
CTCGAGGCCA CCCGGGCCAA AATTTATCAA ATTGACACTT TATGCTTCCG GCTCGTATAC        60
TGTCGACAAT TGTGAGCGGA TAACAATTTC ACACAGAATT C                           101
```

PROMOTERS FOR GENE EXPRESSION

FIELD OF THE INVENTION

This invention relates to the art of genetic engineering as applied to bacterial hosts. More particularly, to expression systems for production of proteins in bacterial hosts.

BACKGROUND OF THE INVENTION

The advent of recombinant DNA technology has enabled the production of various naturally occurring and synthetic proteins in organisms such as bacteria, fungi, yeast and mammalian cells. In general it involves the insertion of genes that encode a desired protein into a host organism, and utilizing the host's cellular machinery to express the gene.

Recombinant DNA technology is continually developing to achieve production of proteins in commercially acceptable yields. A limiting factor in recombinant production of proteins is the rate at which the gene encoding the desired protein is expressed. In particular, it has been found that the promoter region of a gene is critical in the transcription process of gene expression. An efficient promoter such as the trp promoter found in E. coli, binds tightly to DNA-directed RNA polymerase to initiate transcription of the gene in generating mRNA. A less efficient promoter such as the lac promoter binds RNA polymerase less tightly, resulting in a lower rate of mRNA generation.

The trp promoter has been widely used in the production of heterologous proteins because of its ability to initiate transcription. Despite its efficiency, an inherent shortcoming of the trp promoter is that it is not easily controlled. Specifically, the trp promoter is not fully repressible, i.e. it can drive transcription before the host is grown in culture to a phase appropriate for protein production. Another widely used promoter is lac which is less efficient than trp, however is more controllable.

To develop more efficient promoters, functional components of different promoters have been combined, for instance those described in U.S. Pat. No. 5,362,646. In one example, portions of the phage T7 promoter $A_1$ ($P_{A1}$) were combined with two lac operators. Specifically, the spacer region between the so called –35 and –10 regions of the T7 promoter was replaced with a modified lac operator sequence, and to control the resulting promoter hybrid, a second lac operator was introduced downstream. The resulting promoter/operator system which is incorporated on the commercially available pUHE plasmids was found to initiate transcription efficiently upon induction and yet is highly repressed before induction.

Another promoter described by Tsung et al (Proc. Natl. Acad. Sci. USA, 1990, 87:5940) comprises the efficient trp –35 region, the –10 region from the highly efficient lppP–5 promoter (a variant of lpp promoter) and a spacer derived from the lac promoter. This promoter was shown to be so highly efficient in initiating transcription as to result in cell lethality.

While various promoters have allowed improved yields of proteins in microbial hosts, there still remains a need for promoters that drive production of commercially valued proteins more efficiently.

SUMMARY OF THE INVENTION

According to an aspect of the present invention, there is provided a novel recombinant DNA construct useful for expressing a protein in a bacterial host. The construct comprises a coding region for a protein and linked operably therewith, a control region comprising a promoter having a DNA sequence selected from:

5'-TTGACAACATAAAAAACTTTGTGTTATACT-3'; [SEQ ID NO:1]

and

5'-TTGACACTTTATGCTTCCGGCTCGTATACT-3'. [SEQ ID NO:2]

In another aspect, there is provided a novel expression vector that incorporates the constructs of the invention for use in obtaining bacterial host cell transformants that efficiently express the DNA coding for a protein of interest.

5'-TTGACAACATAAAAAACTTTGTGTTATACT-3'; [SEQ ID NO:1]

and

5'-TTGACACTTTATGCTTCCGGCTCGTATACT-3'. [SEQ ID NO:2]

BRIEF DESCRIPTION OF THE DRAWINGS

FIG. 2 illustrates the nucleotide sequence [SEQ ID NO:12] of a DNA construct according to the invention comprising a promoter and operator region.

FIG. 3 illustrates the nucleotide sequence [SEQ ID NO:13] of a DNA construct according to the invention comprising a promoter and operator region.

DETAILED DESCRIPTION OF THE INVENTION

Figure 1:
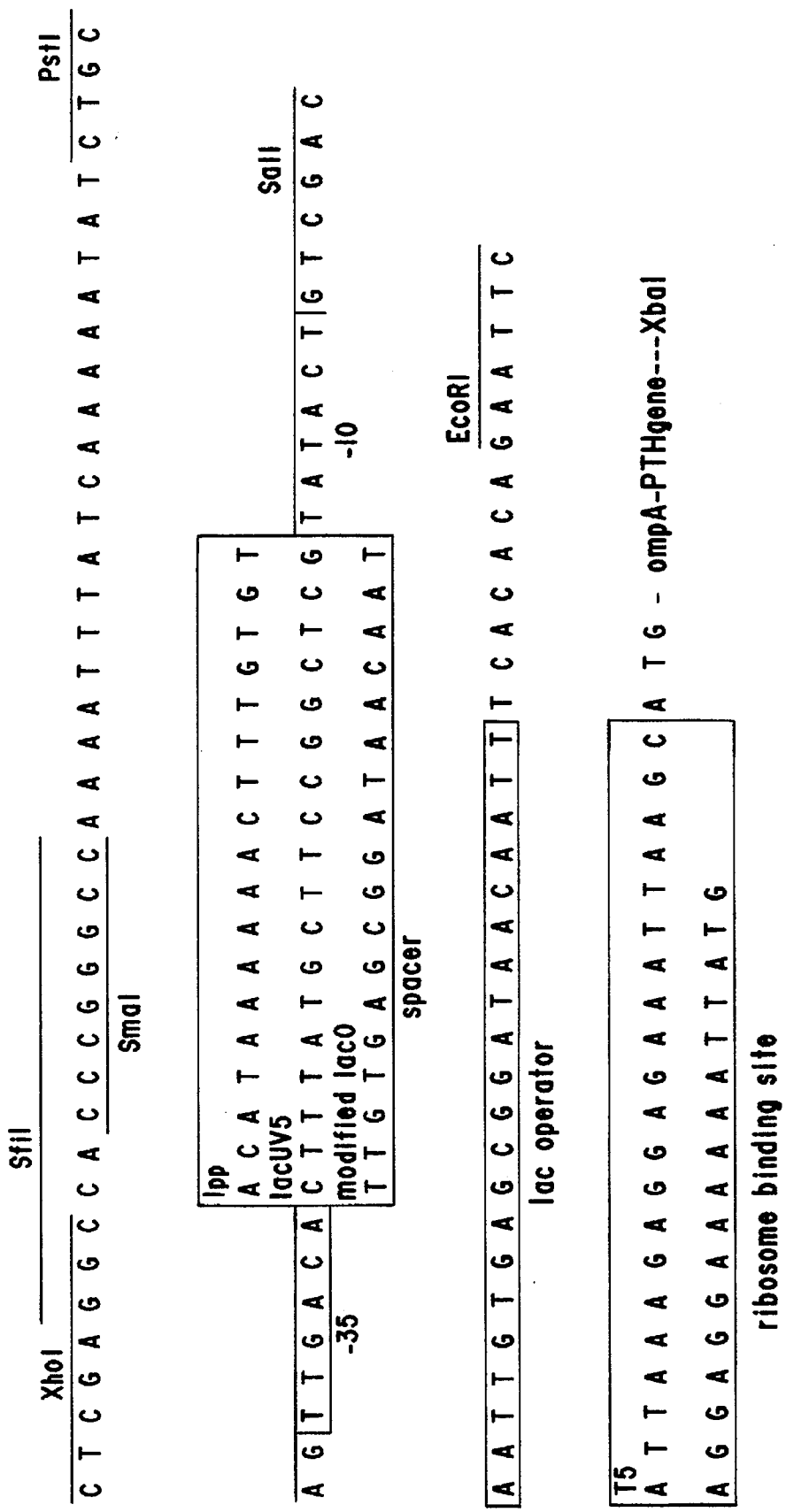
FIG. 1 illustrates the nucleotide sequences [SEQ ID NOS:6–11] and a schematic representation of expression cassettes incorporating recombinant DNA constructs in accordance with the invention.

The present invention provides DNA sequences useful in driving DNA expression with high efficiency in bacterial hosts such as E. coli. The use of expression vectors comprising these sequences provides a valuable means for achieving increased production of expressible proteins, both endogenous and heterologous. In one aspect of the invention, there is provided a novel recombinant DNA construct useful for expressing a protein in a bacterial host. The construct comprises a coding region for the protein operably linked with a control region comprising a promoter to enable expression of said protein in the host, wherein the promoter comprises a DNA sequence selected from:

5'-TTGACAACATAAAAAACTTTGTGTTATACT-3'; [SEQ ID NO:1]

and

5'-TTGACACTTTATGCTTCCGGCTCGTATACT-3'. [SEQ ID NO:2]

These promoters have in common a –35 region of the consensus sequence TTGACA and a –10 region of the sequence TATACT. The spacer sequence, i.e. the sequence of 18 bases which is intervening, can according to the invention be either the sequence ACAT-AAAAAACTTTGTGT [SEQ ID NO:3] or CTTTATGCT-TCCGGCTCG [SEQ ID NO:4] and more preferably the sequence ACATAAAAAACTTTGTGT[SEQ ID NO:3]. Accordingly, the invention provides in a preferred embodiment, DNA constructs in which DNA coding for a desired protein is linked operably under expression control to a promoter of the sequence 5'-TTGACAA-CATAAAAAACTTTGTGTTATACT-3' [SEQ ID NO:1].

Those skilled in the art will appreciate that the promoters of the invention constitute an essential one of the components required within the region functional to drive expression. and can be inserted using standard procedures into any suitable expression vector which can replicate in Gram –ve or +ve bacteria. More particularly, and to form a gene expression control region, the present promoters will be incorporated with such other control elements as are typically required for that expression, including a ribosome binding site and in embodiments of the invention, an operator that functions to control promoter function. These components are necessarily arranged relative to each other as required for expression to occur according to well understood principles of gene expression.

In an embodiment of the invention, the control region of the construct incorporates an operator. Operators that can used include all that are directly inducible by chemical inducers. Examples of operators which are directly inducible include lactose, galactose, tryptophan and tetracycline operators (see Miller et al "The Operon" , Cold Spring Harbour Laboratory, 1980 and Hillen et al, J. Mol. Biol., 1984, 172:185). Preferred operators are highly repressible so that expression of DNA coding for the protein can be controlled. In a specific embodiment, the control region comprises the lac operator (FIG. 1) which prevents expression from the promoter in the absence of inducer isopropyl-β-D-thiogalactopyranoside (IPTG).

The control region further comprises a ribosome binding site (RBS) sequence to facilitate the binding of ribosomes to the mRNA transcript and thereby initiate the translation of the RNA coding region to generate the protein. Suitable ribosome binding sites include lac, T5, In a preferred embodiment the RBS is a sequence derived from the T5 phage RBS having the sequence 5'-ATTAAAG-AGGAGAAATTAAGC-3' [SEQ ID NO:5].

The control region of constructs according to the present invention are operably linked with a coding region for an endogenous or heterologous proteins. By the term "heterologous protein" is meant a polypeptide or protein which, although not naturally produced by the bacterial host, is expressed by this host when suitably transformed with DNA coding for the protein, such as genomic DNA, cDNA and synthetic DNA. Among the proteins that may be produced using the system herein described include, but are not limited to, hormones such as parathyroid hormone (PTH), glucagon or fragments thereof such as GLP-1 and GLP-2; growth factors such as epidermal growth factor (EGF); and lymphokines such as interleukin-6 and -8 (IL-6, -8). In order for isolation of the authentic form of the protein, i.e. protein without an additional N-terminal Met residue, fusion proteins may also be produced which are cleaved subsequent to expression. For example, DNA encoding a protein may be preceded by DNA encoding a signal peptide, such as the E. coli outer membrane protein ompA. In this instance the expressed gene yields a fusion protein comprising a Met residue followed by the ompA signal peptide which is followed by the desired protein. The signal peptide carries the fusion protein through the intermembrane of the bacterium where the signal peptide is cleaved. Other signal peptides which may be used include alkaline phosphatase and protein A from Streptococcus. Alternatively, a fusion protein may be synthesized and cleaved in a separate procedure to yield the desired protein. For example glutathione-S-transferase (GST) may be cleaved from a desired protein with thrombin or factor Xa.

In a specific embodiment of the invention, the coding region comprises DNA encoding human PTH, the amino acid sequence of which is described by Hendy et al (Proc. Natl. Acad. Sci. USA, 1981, 78:7365). In the examples herein described, the DNA sequence coding for PTH was immediately preceded in reading frame with the ompA signal peptide.

The preferred recombinant DNA constructs illustrated in FIG. 1, having the lpp or lacUV5 spacer, were produced from a single-stranded oligonucleotide synthesized by the phosphoramidite method. The gel-purified strand comprising the sequences from the XhoI to EcoRI restriction site was then used as a initial PCR target and was PCR amplified into a double stranded DNA fragment using complementary single stranded DNA oligonucleotides which hybridized specifically to the ends of either the initial oligonucleotide sequence shown or its complementary strand. Thus, the constructs are prepared using standard gene synthesis methodology, as described for example by Maniatus ("Molecular Cloning" Cold Spring Harbour Laboratories, 1982) and Innis et al ("PCR Protocols, A Guide to Methods and Applications").

In another aspect of the invention there is provided expression vectors useful for producing bacterial host cell transformants which incorporate a recombinant DNA construct according to the invention. DNA constructs according to the invention may be incorporated as a "cassette" into a vector, preferably a plasmid vector, by established techniques. Generally, a vector is cleaved at restriction sites that correspond with restriction sites on either end on the cassette. The cassette is then introduced by ligating the ends to the complementary cleaved sites on the vector.

Although phage vectors can be use, plasmid vectors are preferred such as the pUC series of plasmids. Once incorporated on a suitable vector, the resulting plasmid may be amplified in a host to provide amounts sufficient for subsequent cloning work. It will be appreciated that DNA coding for the selected protein is conveniently incorporated on the plasmid with multiple cloning sites provided thereon, using standard cloning/ligation methods. Also, a plasmid will necessarily incorporate an origin of replication and most desirably will incorporate a marker such as the ampicillin or tetracycline resistance genes to allow the selection of transformed cells.

Once DNA coding for the desired protein is incorporated on the vector, a selected bacterial host is transformed therewith using standard calcium chloride mediated transformation techniques. Suitable bacterial hosts include gram negative bacteria such E.coli and Salmonella. Preferably the host is a commercially available E. coli strain and most preferably JM101 and derivatives thereof.

When the controlling region of the DNA construct comprises the lac operator, as described in more detail hereinafter, the transformed host strain should be capable of expressing, preferably over-producing, the lacI product so that promoter function and hence expression of the protein, can be regulated. The need for lacI overproduction by the transformant can be met, according to one embodiment of the invention, by using hosts that already harbour the lacI$^q$ gene responsible for overproduction of the lacI product. LacI over-producing strains of E. coli that may be employed as host include the JM series of strains available from Clontech Laboratories Inc., Calif., USA. Specific host strains suitable for use include JM101, JM105 and JM107.

The need for lacI overproduction in the transformant may alternatively be met by incorporating the lacI$^q$ gene on vectors of the invention. Since, in this situation, the overproduction of lacI is mediated by the vector, any of a variety of commercially available bacterial host strains may be employed, including *E. coli* strains DH1, RR1, C600, CMK603 and EB505. The lacI$^q$ gene to be incorporated on the vector may be obtained as a 1.2 kb HindIII fragment of plasmid pMMB22 (described by Bagdasarian et al (Gene, 1983, 26:273) and then incorporated non-disruptively at any site on the plasmid vector.

To enhance the stability of inheritance of vectors, in particular plasmids, from the strain originally transformed to its progeny, a partition element (par) functional in *E. coli* may also be incorporated on the vector. One such par element may be liberated from pSC101 as a 380bp HincII/AvaI fragment and then cloned into a suitable site on the vector.

Following transformation, bacterial hosts harbouring the excretion vector are cultured in a culturing medium most appropriate for the selected host. For *E. coli*, LB broth or 2YT medium (yeast extract/tryptone) can be used to culture those strains herein preferred. Selective pressure for plasmid transformants should be maintained by providing a cytotoxic agent which kills the untransformed host strain.

For example, a transformant with a plasmid harbouring the gene for tetracycline resistance should be cultured in medium containing tetracycline. Medium concentrations of tetracycline around 5–15µg/mL are suitable.

The promoter on the construct is preferably regulatable through binding of a repressor molecule to an operator located adjacent to the promoter in the control region. In a preferred embodiment, the lacI gene product binds to a lac operator located adjacent the promoter. In this instance, binding of lacI product represses the promoter, lowering expression levels of coding DNA under its control. To raise expression levels, the chemical IPTG (isopropyl-β-D-thiogalactopyranoside), which binds the lacI and derepresses the promoter, is added to the culture medium to derepress the promoter and induce expression. Suitably, IPTG is added to the culture medium when the cells have reached mid log growth phase.

To determine the optimum density to which cultures should be grown to realize maximum yield of the desired protein, trials can be conducted and protein levels assayed in a time-course experiment. In general, reasonable yields of protein may be recovered once cells reach mid log phase, although greater amounts of protein can be expected to accumulate within about 4–5 hours thereafter.

The desired protein can be purified by techniques established in the art as being appropriate for that protein. In a specific embodiment of the invention, expressed PTH is excreted beyond the periplasmic space and into the culture medium where it is recovered directly. When protein is excreted, the spent medium can be isolated using biochemical techniques that reflect the nature of the protein in terms of its molecular size, net charge, isoelectric point, et. The medium may be concentrated first such as by lyophilization. Further, when antibodies are available or a natural ligand for the protein is available, affinity columns may be use.

Specific embodiments of the invention are now exemplified with reference to the drawings.

EXAMPLE 1

In its mature form, PTH is an 84-amino acid peptide that acts in humans to raise blood calcium and increase bone resorption. DNA coding for a PTH analogue, bearing an N-terminal methionine residue was synthesized using the established techniques and according to the amino acid sequence published by Hendy et al., supra.

Preferred recombinant DNA constructs incorporating promoter #1 and #2 as well as reference promoters #3 and #4, illustrated in FIG. 1, to which reference is now made were produced from a single-stranded oligonucleotide synthesized by the phosphoramidite method. The gel-purified strand comprising the sequences from the XhoI to EcoRI restriction site was then used as a initial PCR target and was PCR amplified into a double stranded DNA fragment using complementary single stranded DNA oligonucleotides which hybridized specifically to the ends of either the initial oligonucleotide sequence shown or its complementary strand. Thus, the constructs are prepared using standard gene synthesis methodology, as described for example by Maniatus ("Molecular Cloning" Cold Spring Harbour Laboratories, 1982) and Innis et al ("PCR Protocols, A Guide to Methods and Applications").

The constructs were then cloned into a pUC18 derived plasmid which confers tetracycline resistance in place of ampicillin resistance. A JM101 derived *E. coli* host strain was then transfected according established techniques (see Maniatus et al "Molecular Cloning", Cold Spring Harbour Laboratory, 1982)

EXAMPLE 2

Expression of Transformed Host

The transformants containing the PTH vectors were cultured overnight at 30° C. in 2YT broth containing 0.5% glucose and tetracycline and then inoculated into fresh medium of the same composition, with continued culturing at 30° C. until reaching mid log phase. Cultures were then induced (1mM IPTG) at 1 hour growth intervals, aliquots of culture were withdrawn and fractionated to produce samples of culture medium to identify excreted PTH products using a standard Allegro assay. The results of these assays are provided in Table 1 below:

TABLE 1

| | Promoter | | | | Max PTH (mg/L) |
|---|---|---|---|---|---|
| # | −35 region | spacer | −10 region | RBS | 6–8 hrs |
| 1 | trp | lpp | lppP-5 | T5 | 245 |
| | | | | lac | 148 |
| 2 | trp | lacUV5 | lppP-5 | T5 | 121 |
| | | | | lac | 10 |
| 3 | trp | lacO | lppP-5 | T5 | 50 |
| | | | | lac | 5 |
| 4 | T7 | lacO | T7 | T5 | 100 |
| | | | | lac | 10 |

Results of the Allegro assay indicate that the promoters incorporating the 18 bp lpp and lacUV5 sequences facilitate enhanced levels of heterologous PTH protein. Promoter #1 and #2 compare favourably to promoter #3 wherein the spacer was substituted with a modified lac operator sequence (lacO); and promoter #4 wherein the −35 and −10 regions are from phage T7 and the spacer is iacO promoter. Studies with the same promoters expressing the gene coding for chloramphenicol acetyl transferase (CAT) showed similar results of enhanced expression for promoters #1 and #2. Also, it was noted that each of the promoters studied exhibited enhanced protein yield when combined with the T5 RBS in comparison to the lac derived RBS.

We claim:

1. A recombinant DNA construct which expresses a protein in a bacterial host cell, the construct comprising a coding region for the protein operably linked with a control region comprising a promoter which promotes expression of said protein in the host cell, wherein the promoter comprises a DNA sequence selected from the group consisting of SEQ ID NO:1 and SEQ ID NO:2.

2. The recombinant DNA construct according to claim 1, wherein said promoter comprises the DNA sequence of SEQ ID NO:1.

3. The recombinant DNA construct according to claim 1, wherein said bacterial host cell is an *E. coli* cell.

4. The recombinant DNA construct according to claim 3, wherein said control region further comprises an operator for regulating expression of the protein.

5. The recombinant DNA construct according to claim 4, wherein the operator is the lac operator.

6. The recombinant DNA construct according to claim 5, wherein the protein is human parathyroid hormone.

7. The recombinant DNA construct according to claim 6, further comprising DNA coding for an OmpA signal peptide in reading frame with the coding region, thereby promoting secretion of the protein to the periplasm of the host cell.

8. The recombinant DNA construct according to claim 3, wherein the control region further comprises a T5 ribosome binding site having the DNA sequence of SEQ ID NO:5.

9. The recombinant DNA construct according to claim 3, wherein the control region comprises the sequence of SEQ ID NO:12.

10. The recombinant DNA construct according to claim 3, wherein the control region comprises the sequence of SEQ ID NO:13.

11. A vector comprising the recombinant DNA construct according to claim 1.

12. A vector comprising the recombinant DNA construct according to claim 4.

13. A vector comprising the recombinant DNA construct according to claim 5.

14. A vector comprising the recombinant DNA construct according to claim 6.

15. A vector comprising the recombinant DNA construct according to claim 7.

16. A vector comprising the recombinant DNA construct according to claim 8.

17. A vector comprising the recombinant DNA construct according to claim 9.

18. A vector comprising the recombinant DNA construct according to claim 10.

19. The vector according to claim 11, further comprising the $lacI^q$ gene.

20. The vector according to claim 11, further comprising the par element.

* * * * *